(12) United States Patent
Tseng et al.

(10) Patent No.: US 10,675,260 B2
(45) Date of Patent: Jun. 9, 2020

(54) METHODS AND PHARMACEUTICAL COMPOSITIONS FOR PREVENTING OR TREATING IMMUNOINFLAMMATORY DERMAL DISORDERS

(71) Applicant: TWi Biotechnology, Inc., Taipei (TW)

(72) Inventors: Po-Yuan Tseng, Taipei (TW); Wei-Shu Lu, New Taipei (TW); Carl Oscar Brown, III, San Diego, CA (US); I-Yin Lin, III, Taipei (TW); Chen-En Tsai, Taipei (TW); Chih-Kuang Chen, Taipei (TW)

(73) Assignee: TWi Biotechnology, Inc., Taipei (TW)

(*) Notice: Subject to any disclaimer, the term of this patent is extended or adjusted under 35 U.S.C. 154(b) by 66 days.

(21) Appl. No.: 15/875,750

(22) Filed: Jan. 19, 2018

(65) Prior Publication Data

US 2018/0200235 A1    Jul. 19, 2018

Related U.S. Application Data

(60) Provisional application No. 62/448,219, filed on Jan. 19, 2017.

(51) Int. Cl.
| | | |
|---|---|---|
| *A61K 31/192* | (2006.01) | |
| *A61P 17/00* | (2006.01) | |
| *A61K 31/235* | (2006.01) | |
| *A61K 31/225* | (2006.01) | |
| *A61K 9/06* | (2006.01) | |

(52) U.S. Cl.
CPC .............. *A61K 31/192* (2013.01); *A61K 9/06* (2013.01); *A61K 31/225* (2013.01); *A61K 31/235* (2013.01); *A61P 17/00* (2018.01)

(58) Field of Classification Search
CPC ....... A61K 9/06; A61K 31/225; A61K 31/192
See application file for complete search history.

(56) References Cited

U.S. PATENT DOCUMENTS

| | | | |
|---|---|---|---|
| 6,610,750 B1 * | 8/2003 | Charbit ................. | A61K 31/19 514/734 |
| 9,427,432 B2 | 8/2016 | Wang et al. | |
| 2012/0165357 A1 | 6/2012 | Hung et al. | |
| 2017/0000732 A1 * | 1/2017 | Chen ....................... | A61K 9/06 |

OTHER PUBLICATIONS

Benedetto et al, JID (2012), vol. 132, pp. 949-963. (Year: 2012).*
Schmidt et al, J. Dermatol. Science, vol. 11 (1996), pp. 142-147. (Year: 1996).*
International Search Report and Written Opinion for corresponding PCT application No. PCT/US18/14366 dated May 4, 2018.
Wojnarowska, F et al., "Guidelines for the management of bullous pemphigoid", British Journal of Dermatology, vol. 147, Aug. 9, 2002, pp. 214-221.

* cited by examiner

*Primary Examiner* — Craig D Ricci
*Assistant Examiner* — Janet L. Coppins
(74) *Attorney, Agent, or Firm* — Wood, Phillips, Katz, Clark & Mortimer

(57) ABSTRACT

A method for preventing or treating immunoinflammatory dermal disorders is provided. Also provided is a pharmaceutical composition for preventing or treating immunoinflammatory dermal disorders.

8 Claims, 6 Drawing Sheets
(6 of 6 Drawing Sheet(s) Filed in Color)

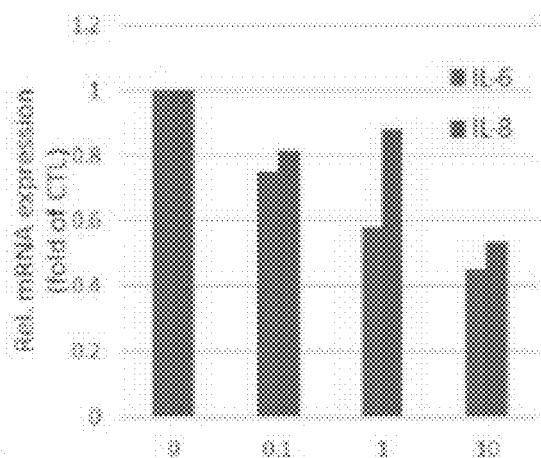
Fig. 4a Clobetasol propionate
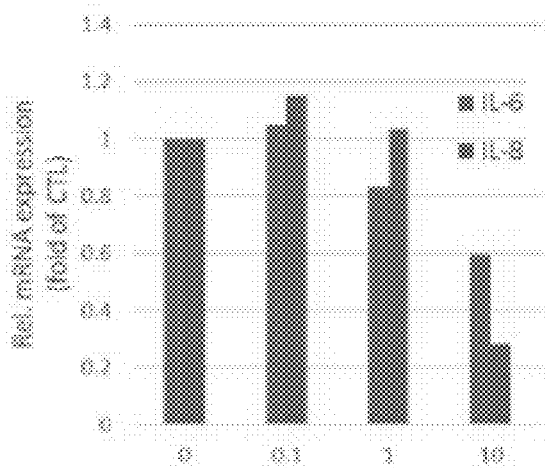
Fig. 4b Diacerein
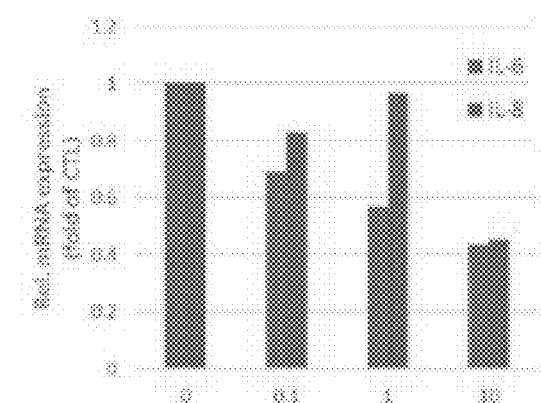
Fig. 4c Berberine Control (no IgG treated)      Healthy-IgG treated BP-IgG treated BP-IgG + berberine 0.1 µM    BP-IgG + berberine 1 µM    BP-IgG + berberine 10 µM Control (no IgG treated)  Healthy-IgG treated BP-IgG treated BP-IgG + diacerein 0.1 μM   BP-IgG + diacerein 1 μM   BP-IgG + diacerein 10 μM

METHODS AND PHARMACEUTICAL COMPOSITIONS FOR PREVENTING OR TREATING IMMUNOINFLAMMATORY DERMAL DISORDERS

BACKGROUND OF THE INVENTION

Field of the Invention

The present invention relates to methods and pharmaceutical compositions for preventing or treating immunoinflammatory dermal disorders.

Background of the Invention

Immunoinflammatory skin disorders encompass a variety of conditions, including autoimmune skin diseases, proliferative skin diseases, and inflammatory dermatoses. Immunoinflammatory skin disorders result in the destruction of healthy tissue by an inflammatory process, dysregulation of the immune system, and unwanted proliferation of cells.

Bullous pemphigoid (BP) is the most common autoimmune blistering skin disease, and it commonly develops in the elderly, with onset usually in the late 70s and a substantial increase of incidence in people older than 80 years.

It is suggested that pathogenesis of BP includes complement activation, mast cell degranulation, recruitment and activation of neutrophils and eosinophils, and release of basement membrane zone (BMZ)-degrading proteinases from these effector cells.

Although the precise sequence of these events is largely unknown, it has been proposed that one of the first steps leading to blister formation in BP comprises autoantibodies (autoAbs) targeting the hemidesmosomal transmembrane protein BP180, also known as collagen XVII (COL17), which is thought to be the major autoantigen (autoAg) within the dermal-epidermal junction. Following binding of NC16A, the extracellular domain of BP180, the autoAbs initiate Fc receptor-independent events leading to the release of interleukin (IL)-6 and IL-8 from basal keratinocytes in a dose- and time-dependent manner. In addition, it has been reported that the binding of autoAbs and BP180 induces BP180 internalization, which plays a key role in the initiation of BP disease pathogenesis (*Bullous Pemphigoid IgG Induces BP180 Internalization via a Macropinocytic Pathway*, Hiroyasu et al, *The American Journal of Pathology*, Vol. 182, No. 3, March 2013, p 828-840).

The inventors of the present application found that diacerein and/or berberine are able to inhibit the production of pro-inflammatory cytokines related to immunoinflammatory dermal disorders as well as BP180 internalization, and thus have treatment potential for immunoinflammatory dermal disorders, especially BP.

BRIEF SUMMARY OF THE INVENTION

In one embodiment, this invention provides a method for preventing or treating immunoinflammatory dermal disorders, comprising administering to a subject in need thereof a pharmaceutical composition comprising a therapeutically effective amount of berberine or a biologically equivalent analogue of berberine or a pharmaceutically acceptable salt thereof.

In another embodiment, this invention provides a method for preventing or treating immunoinflammatory dermal disorders, comprising administering to a subject in need thereof a pharmaceutical composition comprising a therapeutically effective amount of a compound selected from the group consisting of diacerein, rhein, monoacetylrhein, and salts or esters or prodrugs thereof.

The invention also provides a pharmaceutical composition for preventing or treating immunoinflammatory dermal disorders, comprising a therapeutically effective amount of berberine or a biologically equivalent analogue of berberine or a pharmaceutically acceptable salt thereof.

The invention also provides a pharmaceutical composition for preventing or treating immunoinflammatory dermal disorders, comprising a therapeutically effective amount of a compound selected from the group consisting of diacerein, rhein, monoacetylrhein, and salts or esters or prodrugs thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4a is a statistical bar graph showing the inhibitory effects of clobetasol propionate on mRNA production of IL-6 and IL-8;

FIG. 4b is a statistical bar graph showing the inhibitory effects of diacerein on mRNA production of IL-6 and IL-8;

FIG. 4c is a statistical bar graph showing the inhibitory effects of berberine on mRNA production of IL-6 and IL-8;

DETAILED DESCRIPTION OF THE INVENTION

Figure 1A:
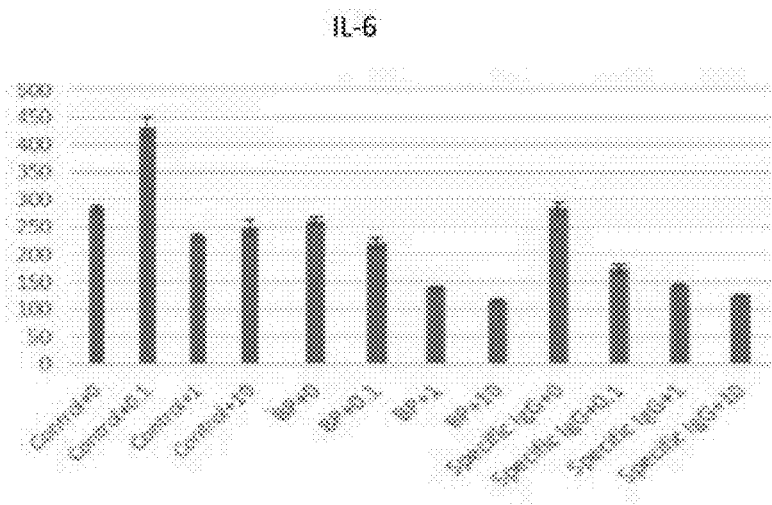
FIG. 1a is a statistical bar graph showing the inhibitory effects of clobetasol propionate on production of IL-6.

The term "therapeutically effective amount," as used herein, refers to an amount that alleviates or reduces one or more symptoms of a disease in at least one or more patients.

The term "diacerein or its analogs," as used herein, refers to diacerein, rhein, monoacetylrhein, or a pharmaceutically acceptable salt or ester or a prodrug thereof.

The term "prodrug," as used herein, refers to any compound that can be metabolized into its parent compound and exerts its physiological function in form of the parent compound within the body.

Unless otherwise stated herein, the terms "a (an)", "the" or the like used in this specification (especially in the Claims hereinafter) shall be understood to encompass both the singular form and the plural form.

Chemically, rhein is 9, 10-dihydro-4, 5-dihydroxy-9, 10-dioxo-2-anthracene carboxylic acid having a structure of Formula (I), and one of its prodrugs, diacerein, is 4, 5-bis (acetyloxy) 9, 10-dihydro-4, 5-dihydroxy-9, 10-dioxo-2-anthracenecarboxylic acid having a structure of Formula (II). Diacerein is entirely converted into rhein before reaching the systemic circulation, and exerts its physiological function in form of rhein within the body.

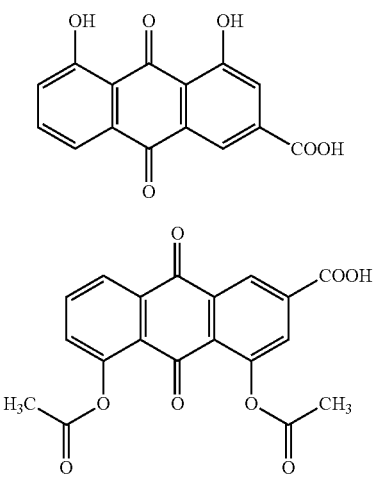

Diacerein is an anti-inflammatory agent widely used in the treatment of osteoarthritis, which has been demonstrated to inhibit interleukin-1 (IL-1) signaling. Presently, diacerein capsules are available in 50 mg strength and are marketed under various trade names in different countries, including Art 50®, Artrodar®, etc.

Berberine (Natural Yellow 18, 5,6-dihydro-9,10-dimethoxybenzo(g)-1,3-benzodioxolo (5,6-a) quinolizinium) is an isoquinoline alkaloid present in herb plants, such as coptis (Coptidis rhizome), phellodenron, Scutellaria baicalensis, Mahonia aquifolium and berberis. Berberine and its derivatives have been found to have antimicrobial and antimalarial activities. It can act against various kinds of pathogens such as fungi, saccharomycete, parasite, bacterium and virus.

The inventors of the present application found that diacerein and berberine are able to inhibit the production of pro-inflammatory cytokines related to immunoinflammatory dermal disorders as well as BP180 internalization, and can be used in the treatment of these disorders. Therefore, the present invention provides a method for preventing or treating immunoinflammatory dermal disorders, comprising administering to a subject in need thereof a pharmaceutical composition comprising a therapeutically effective amount of berberine or a biologically equivalent analogue of berberine or a pharmaceutically acceptable salt thereof.

The biologically equivalent analogue of berberine in the present method includes, but is not limited to, for example, jatrorrhizine, palmatine, coptisine, 9-demethylberberine, 9-demethylpalmatine, 13-hydroyberberine, berberrubine, palmatrubine, 9-O-ethylberberrubine, 9-O-ethyl-13-ethyl-berberrubine, 13-methyldihydroberberine N-methyl salt, tetrahydroprotoberberines and N-methyl salts thereof, and 9-lauroylberberrubine chloride.

Preferably, the pharmaceutically acceptable salt is berberine chloride.

In one embodiment, berberine or the biologically equivalent analogue of berberine or pharmaceutically acceptable salt thereof is the primary pharmaceutically active component in the present method.

In another embodiment, berberine or the biologically equivalent analogue of berberine or pharmaceutically acceptable salt thereof is the only pharmaceutically active component in the present method.

The present invention also provides a method for preventing or treating immunoinflammatory dermal disorders, comprising administering to a subject in need thereof a pharmaceutical composition comprising a therapeutically effective amount of a compound selected from the group consisting of diacerein, rhein, monoacetylrhein, and salts or esters or prodrugs thereof (i.e., diacerein and its analogs).

In one embodiment, the compound is diacerein.

In one embodiment, diacerein and its analogs is the primary pharmaceutically active component in the present method.

In another embodiment, diacerein and its analogs is the only pharmaceutically active component in the present method.

In one embodiment, said therapeutically effective amount of said compound is equivalent to 10 to 200 mg of diacerein base per day.

Preferably, the subject in the present invention is a human.

In one embodiment, said immunoinflammatory dermal disorder is selected from the group consisting of acute febrile neutrophilic dermatosis, dermatomyositis, exfoliative dermatitis, pompholyx, neutrophilic hidradenitis, sterile pustulosis, pruritic urticarial papules and plaques of pregnancy, bullous pemphigoid, pemphigus vulgaris, dermatitis herpetiforms, pemphigoid gestationis, bowel-associated dermatosis-arthritis syndrome, rheumatoid neutrophilic dermatosis, neutrophilic dermatosis of the dorsal hands, balanitis circumscripta plasmacellularis, balanoposthitis, Behcet's disease, erythema annulare centrifugum, erythema dyschromicum perstans, erythema multiforme, granuloma annulare, hand dermatitis, lichen nitidus, lichen planus, lichen sclerosus et atrophicus, lichen simplex chronicus, lichen spinulosus, nummular dermatitis, pyoderma gangrenosum, sarcoidosis, subcorneal pustular dermatosis, urticaria, palmoplantar pustulosis, drug eruption, acute generalized exanthematous pustulosis, contact dermatitis, and transient acantholytic dermatosis.

Preferably, the immunoinflammatory dermal disorder is bullous pemphigoid.

Hereinafter, the present invention will be further illustrated with reference to the following examples. However, these examples are only provided for illustrate purpose, but not to limit the scope of the present invention.

EXAMPLES

[Example 1] Cytokine Production Inhibition Study

The effects of diacerein or berberine to reduce anti-BP180 immunoglobulin G (IgG)-stimulated production of BP-related pro-inflammatory cytokines, IL-6 or IL-8, from human adult skin keratinocytes, HaCaT cells, were studied. Clobetasol propionate, a commonly used corticosteroid to treat BP as well as various other skin disorders, was used as a positive control.

IgG was purified from normal or BP patient blood. Therefore, blood collection from healthy donors or BP patients was involved in the study. Purified IgG was used to stimulate production of pro-inflammatory cytokines such as IL-6 and IL-8 from HaCaT cells.

Blood Collection

Patients treated in the Department of Dermatology of the National Taiwan University Hospital (NTUH) must have a confirmed diagnosis of BP based on typical clinical findings as well as on documentation of detection of linear deposits of IgG and/or C3 at the dermal-epidermal junction by direct immunofluorescence (DIF) microscopy or circulating IgG autoantibodies against BP180 NC16A by enzyme-linked immunosorbent assay (ELISA) (MBL Co Ltd, Nagoya, Japan).

Blood was collected twice from BP patients as well as healthy volunteers. The total amount of blood was 40 mL from healthy donor(s) or BP patient(s) and the maximum to be drawn at a single visit per subject was 20 mL.

Demographics including age, gender, medical history including BP and diagnosis information, and levels of circulating normal IgG anti-BP180, or anti-BP230 IgG autoantibodies were recorded.

The collection of blood samples was approved by the Research Ethics Committee (REC) of NTUH, and informed consent was obtained according to the Declaration of Helsinki.

Expression of BP180-NC16A Protein

The BP180-NC16A expression plasmid was kindly provided by Prof. Hiroshi Shimizu and Prof. Wataru Nishie (Department of Dermatology, Hokkaido University Graduate School of Medicine, Sapporo, Japan). The construct encoding NC16A domain (77 amino acids) was inserted within the MCS of pGEX-6P1 vector. The plasmids were transformed into DH5a competent cells and then the DNA was extracted with the sequence confirmed to be human BP180 NC16A. To obtain large amount of NC16A protein, BL21 was transformed by introducing the plasmid, then NC16A domain protein was expressed using Overnight Express Autoinduction system (Novagen) according to the manufacturer's instruction.

Purification of IgG

Total serum IgG from healthy blood donors (Healthy-IgG) and patients diagnosed with BP (BP-IgG) was isolated using Hitrap Protein A HP column (GE Healthcare Life Sciences). Immunoglobulins were eluted with 0.1M NaPi pH8.0 (equilibration), 0.1M Na-citrate pH6.0 (wash), and 0.1M Na-citrate pH3.0 (elution). Then the concentrated immunoglobulins were further eluted by CNBr-activated Sepharose Column (GE Healthcare Life Sciences) coupled with BP180-NC16A protein and the concentrated specific IgG reactive to NC16A can be isolated (Protein A Elu-NC16A-Elu). Immunoreactivity of the affinity-purified BP IgG preparations was confirmed by anti-BP180-NC16A ELISA (MBL Co Ltd, Nagoya, Japan).

Cell Culture

HaCaT cells (CLS Cell Lines Service, Germany) were cultured in Dulbecco's modified eagle medium (DMEM) medium supplemented with 4.5 g/L glucose, 2 mM L-glutamine and 10% fetal bovine serum. Cells were seeded on 24- or 12-well plates and grown to 80% confluence for the following assays.

Cell Viability or Cytotoxicity Assessment

Exponentially growing cells of passage #3-6 (3000 cells/well in 100 µl medium) were plated in 96-well plates overnight to allow cell attachment (80% confluency) and then exposed to different concentrations of diacerein (0.1, 1, 10 µM) or berberine (0.1, 1, 10 µM) or clobetasol propionate (0.1, 1, 10 µM), and either 2 mg/mL of Healthy-IgG BP-IgG or Specific-IgG at 37° C. for 48 h.

Following drug treatment, the cell culture media were gently removed. Cells were then gently washed three times with warm medium to remove any de-attached and dead cells. Cells were incubated with MTT reagent in cell culture medium at a final concentration of 1.0 mg/mL for 2 h. The quantity of formazan (presumably directly proportional to the number of viable cells) was measured by recording changes in absorbance at 570 nm using an ELISA plate reader.

Pro-Inflammatory Cytokine Measurement

Cytokine measurement was conducted based on previous studies. Briefly, cells were incubated with medium alone or with 2 mg/mL purified BP-IgG or Specific-IgG and cultured in absence or presence of diacerein or berberine or clobetasol propionate (0.1, 1, and 10 µM) and culture supernatants were collected after 48 h of incubation, and stored for analysis at −20° C. IL-6 and IL-8 levels were analyzed in cell culture supernatants by ELISA (BD Biosciences) according to the manufacturer's instructions.

Quantitation of IL-6 and IL-8 mRNA Expression by Quantitative Real-Time Polymerase Chain Reaction IL-6 and IL-8 messenger RNA (mRNA) levels were quantitated using quantitative real-time polymerase chain reaction (qPCR) as reported previously. BP IgG-treated HaCaT cells were cultured with or without diacerein or berberine or clobetasol propionate for 48 h. Total RNA was isolated from cultured HaCaT cells using TRIzol reagent (LifeTechnologies) according to the manufacturer's instruction. Complementary DNA (cDNA) was reverse-transcribed from isolated RNA by incubating 1 µg of RNA with the RevertAid First Strand cDNA Synthesis Kit (Thermo Scientific) following the manufacturer's instructions. Quantitative RT-PCR was performed in a Mastercycler (Eppendorf) using SYBR® Select Master Mix (Life Technologies). PCR mixtures contained 0.5 µM of each forward and reverse primers. Each reaction mixture was subjected to 2 min at 50° C. and 2 min at 95° C. followed by 40 cycles with 15 seconds at 95° C. and 1 min at 60° C. Data were normalized to the housekeeping gene glyceraldehyde-3-phosphate dehydrogenase (GAPDH). The primers used in RT-PCR were as follows: IL-8 messenger RNA (mRNA), forward, 5'-ACC GGA AGG AAC CAT CTC AC-3', and reverse, 5'-AAA CTG CAC CTT CAC ACA GAG-3' and IL-6 messenger RNA (mRNA), forward, 5'-GGT ACA TCC TCG ACG GCA TCT-3', and reverse, 5'-GTG CCT CTT TGC TGC TTT CAC-3' and GAPDH, forward, 5'-ACA ACT TTG GTA TCG TGG AAG G-3', and reverse, 5'-GCC ATC ACG CCA CAG TTT-3'.

Statistical Analysis

Data were analyzed using Student's t test or one-way analysis of variance (ANOVA). A p value <0.05 was considered to indicate a statistically significant difference.

[Results]

A total of 13 subjects were recruited during the study period. Six of them were normal controls, while the other seven subjects were initially diagnosed as having bullous pemphigoid (BP). One (case no. 12) of the 7 BP patients was screen-failure due to negative DIF/IIF findings. Case nos. 1, 2, 3, 4, and 13 had elevated circulating IgG autoantibodies against BP180 NC16A by ELISA.

Large amount of the human NC16A protein was obtained by using GST-Bulk Kit and B-PER Protein Extraction Reagents (Thermo), and then the cleavage of GST-tag was performed by using PreScission Protease system.

To isolate serum IgG from healthy blood donors (Healthy-IgG) and patients diagnosed with BP (BP-IgG), Hitrap Protein A HP column was used and the concentrated immunoglobulins were further eluted by CNBr-activated Sepharose Column coupled with BP180-NC16A protein. The isolated efficiency was demonstrated by relative fold changes among IgG isolated from initial step (Protein A Elu) and the concentrated specific IgG reactive to NC16A (Protein A Elu-NC16A-Elu, that is Specific-IgG), which had the highest purification fold up to 23.46 and 6821 IU/mg of specific IgG.

Keratinocyte cytotoxicity under different concentrations of diacerein, berberine or clobetasol propionate was evaluated by MTT test. Diacerein treatment at 0.1-10 μM had significant cytotoxicity to HaCaT cells with reduced viability to 50%. Treatment with serum samples from healthy controls (Healthy-IgG), BP-IgG or BP Specific-IgG enhanced HaCaT viability up to 250%, but 10 μM of diacerein treatment still significantly reduced HaCaT viability. In contrast, berberine and clobetasol propionate treatment at 0.1-10 μM did not have significant cytotoxicity to HaCaT cells.

Figure 1B:
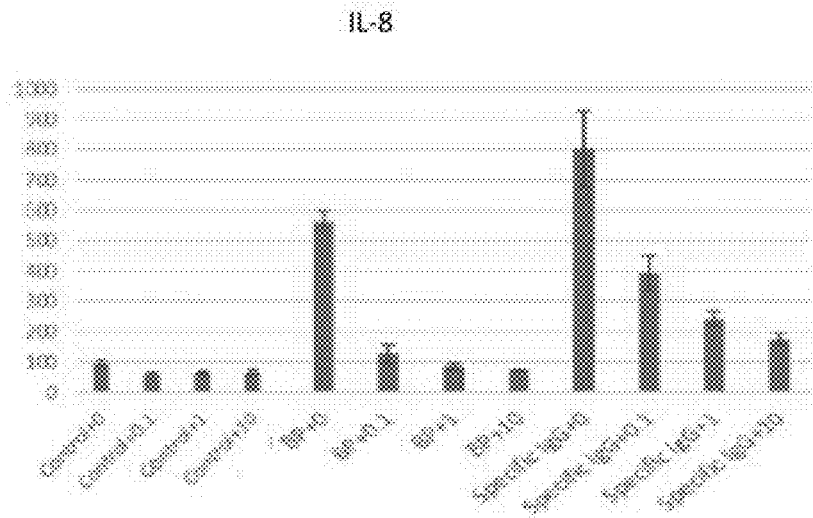
FIG. 1b is a statistical bar graph showing the inhibitory effects of clobetasol propionate on production of IL-8.
Figure 2A:
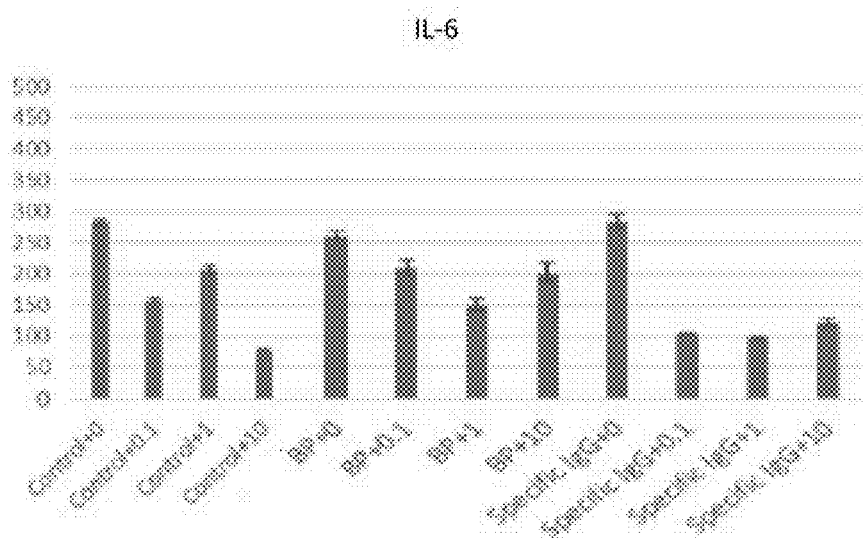
FIG. 2a is a statistical bar graph showing the inhibitory effects of diacerein on production of IL-6.
Figure 2B:
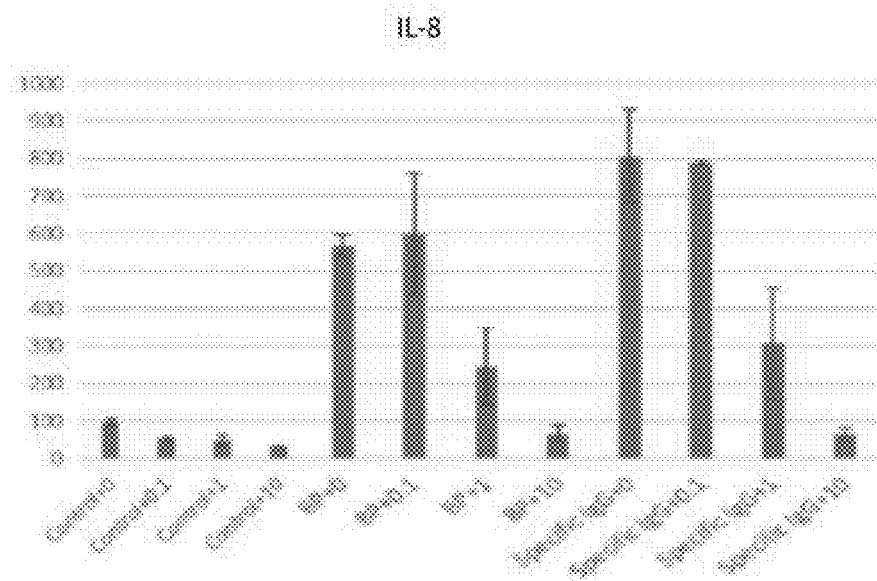
FIG. 2b is a statistical bar graph showing the inhibitory effects of diacerein on production of IL-8.

Changes of IL-6 and IL-8 were examined after the HaCaT cells incubated with medium alone or with 2 mg/mL purified BP-IgG or Specific-IgG with different concentrations of diacerein, berberine or clobetasol propionate (0, 0.1, 1, and 10 μM) and culture supernatants were collected after 48 h of incubation. The positive control treatment, clobetasol propionate, reduced IL-6 (FIG. 1a) and IL-8 secretion (FIG. 1b) in a dose-dependent manner. Diacerein significantly reduced secretion of IL-6 in HaCaT cells treated with specific anti-BP180 IgG (FIG. 2a). In contrast, diacerein at 0.1 μM did not reduce the secretion of IL-8 in HaCaT cells treated with specific anti-BP180 IgG The inhibitory effects of diacerein on IL-8 secretion were noted only at concentrations at 1 or 10 μM (FIG. 2b).

Figure 3A:
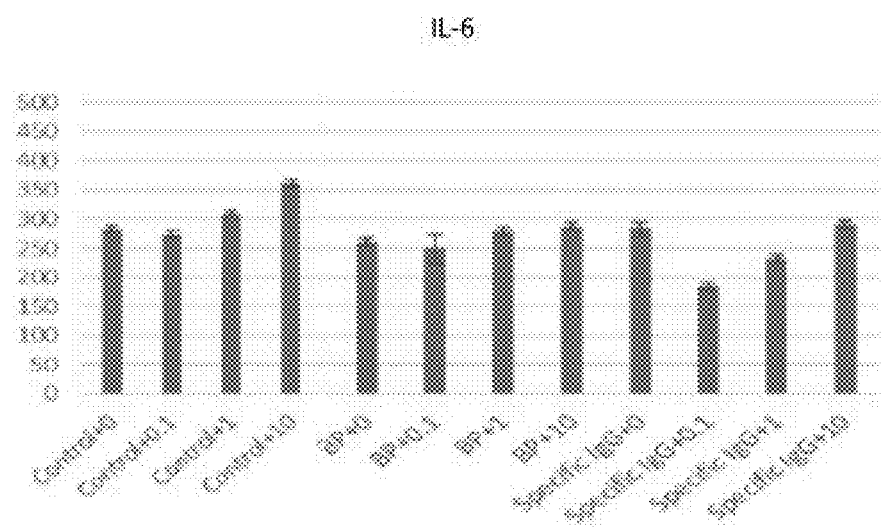
FIG. 3a is a statistical bar graph showing the inhibitory effects of berberine on production of IL-6.
Figure 3B:
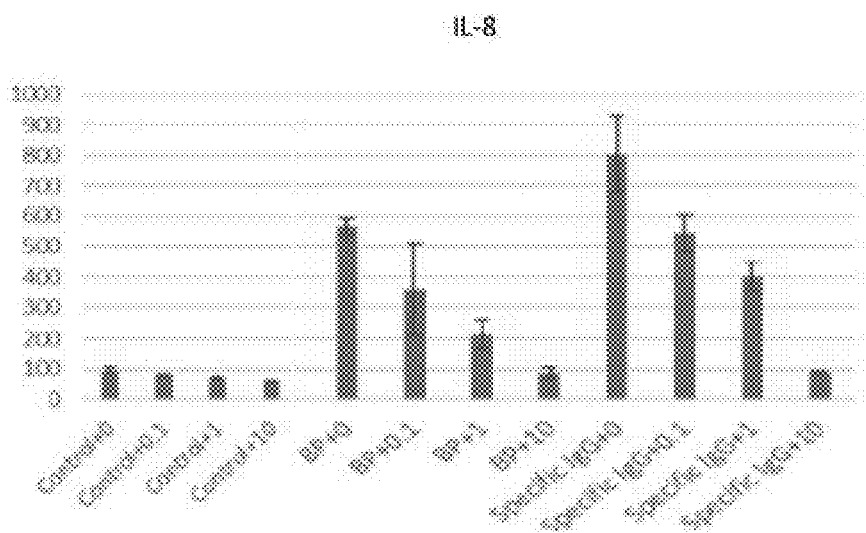
FIG. 3b is a statistical bar graph showing the inhibitory effects of berberine on production of IL-8.

Berberine did not reduce the secretion of IL-6 in HaCaT cells treated with specific anti-BP180 IgG (FIG. 3a). Berberine dose-dependently reduced the secretion of IL-8 in HaCaT cells treated with BP Specific-IgG The inhibitory effects were significantly better in those cells treated with BP Specific-IgG (FIG. 3b).

BP IgG-treated HaCaT cells were cultured with different concentrations (0, 0.1, 1, 10 μM) of diacerein, berberine or clobetasol propionate for 48 h. Total RNA was isolated from cultured HaCaT cells and quantitative RT-PCR (RT-qPCR) analysis was performed. The results showed clobetasol propionate significantly reduced the IL-6 and IL-8 mRNA expression levels (FIG. 4a), while diacerein had dose-dependent inhibitory effects on IL-6 mRNA expression levels, but had inhibitory effects on IL-8 mRNA only at 10 μM (FIG. 4b). In contrast, berberine had dose-dependent inhibitory effects on both IL-6 and IL-8 mRNA expression (FIG. 4c).

The above study shows that diacerein and berberine have inhibitory effects on the production of pro-inflammatory cytokines related to immunoinflammatory dermal disorders, and thus may have treatment potential for immunoinflammatory dermal disorders.

[Example 2] BP180 Internalization Study

BP180 is an important component of hemidesmosome, which keeps keratinocytes attached to the basement membrane of skin. BP180 damage could lead to poor attachment of keratinocytes, and is associated with skin disorders or blistering diseases. BP180 internalization is considered as the key role in the pathogenesis of bullous pemphigoid and thus can be measured for evaluation of this disease. The following study was conducted to evaluate the effects of berberine, diacerein or rhein on autoAbs (BP-IgG) induced BP180 internalization and hemidesmosome disruption in keratinocytes treated with BP-IgG.

Method: Immunofluorescence Studies of BP180 Internalization

For this BP180 internalization study, IgG purification from BP patients and cell culture treated with different IgG and drugs (diacerein or berberine) were performed according to the procedures described in Example 1.

Keratinocytes grown on glass coverslips were fixed in 4% paraformaldehyde, washed thoroughly in PBS, and permeabilized in 0.1% (v/v) Triton X-100 in PBS for 10 minutes. Primary antibodies were overlaid onto the cells, and the preparations were incubated at room temperature for 1 hour. The cells on coverslips were washed with PBS, and fluorescence-conjugated secondary antibodies were applied for 1 hour at room temperature. After being washed with PBS, coverslips were mounted onto slides. The fluorescence color for cell nucleus was dark blue and BP180 was bright green. All preparations were examined by the confocal microscopy.

[Result]

Berberine Treatment

Figure 5A:
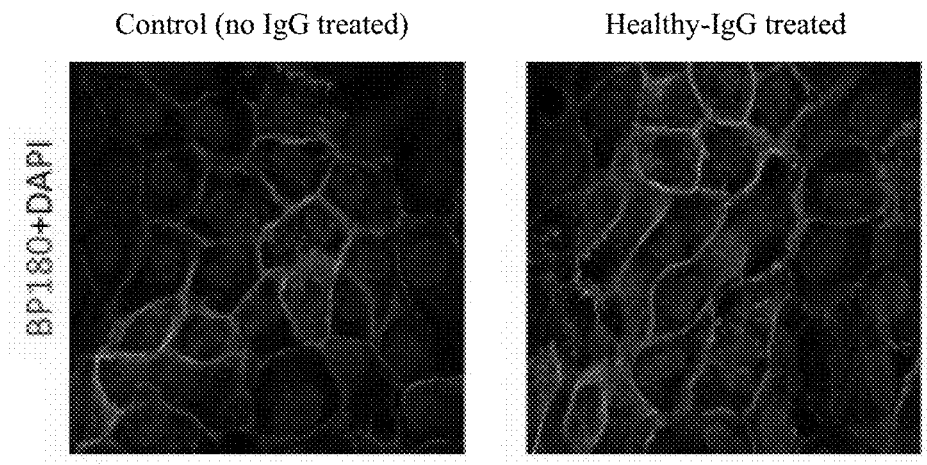
FIG. 5a shows confocal microscopy photographs of keratinocytes stained with fluorescence color (cell nucleus: dark blue; BP180: bright green) and treated with IgG (right panel) and control (left panel; not treated with IgG)
Figure 5B:
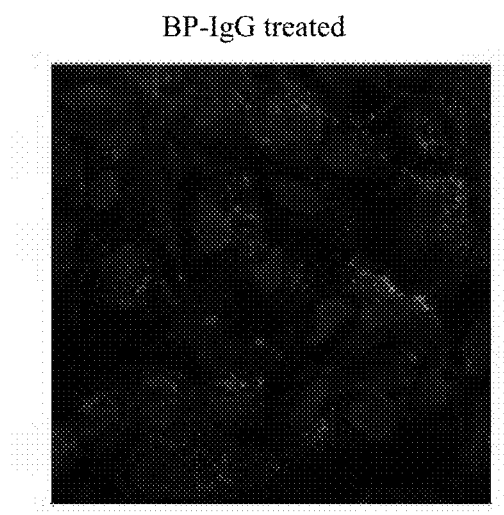
FIG. 5b shows confocal microscopy photographs of keratinocytes stained with fluorescence color and treated with IgG.
Figure 5C:
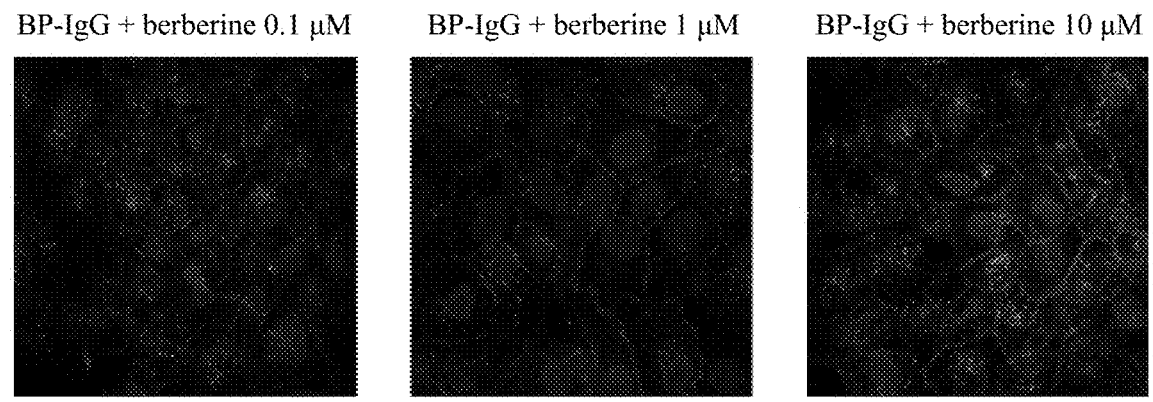
FIG. 5c shows confocal microscopy photographs of keratinocytes stained with fluorescence color and treated with IgG and berberine at different concentrations.

In the control keratinocytes (i.e., not treated by IgG) and keratinocytes treated with IgG from the healthy subjects, immunofluorescence analysis of BP180 (bright green) showed prominent cytoplasmic and membranous localization (FIG. 5(a)). In contrast, membranous localization of BP180 in cells treated with BP-IgG was significantly reduced and appeared more diffuse in the cytoplasm, suggesting occurrence of BP180 internalization and hemidesmosome disruption induced by BP-IgG treatment (FIG. 5(b)). As berberine concentration increased (0.1 to 10 μM), membranous localization of BP180 was restored, suggesting inhibition of BP180 internalization and maintenance of hemidesmosome integrity after berberine treatment (FIG. 5(c)).

Diacerein Treatment

Figure 6A:
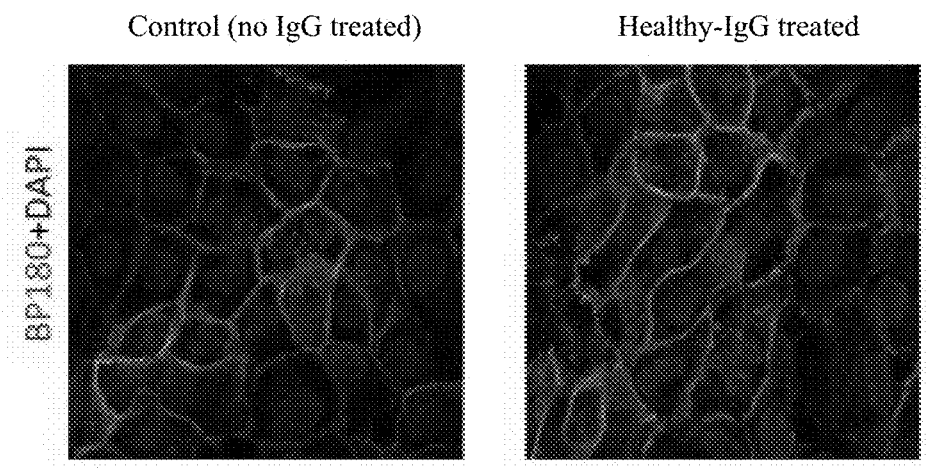
FIG. 6a shows confocal microscopy photographs of keratinocytes stained with fluorescence color and treated with IgG (right panel) and control (left panel; not treated with IgG)
Figure 6B:
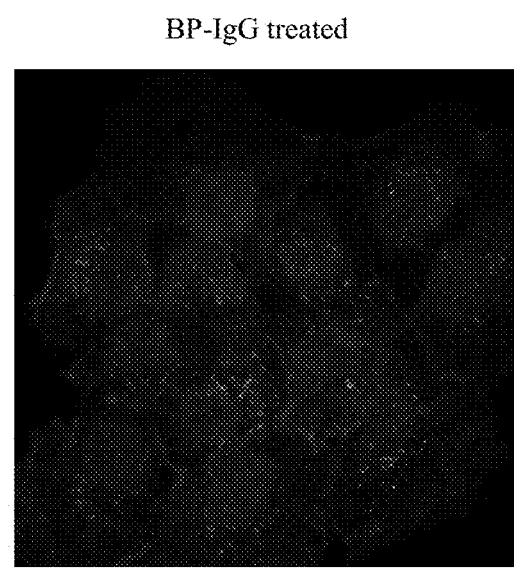
FIG. 6b shows confocal microscopy photographs of keratinocytes stained with fluorescence color and treated with IgG.
Figure 6C:
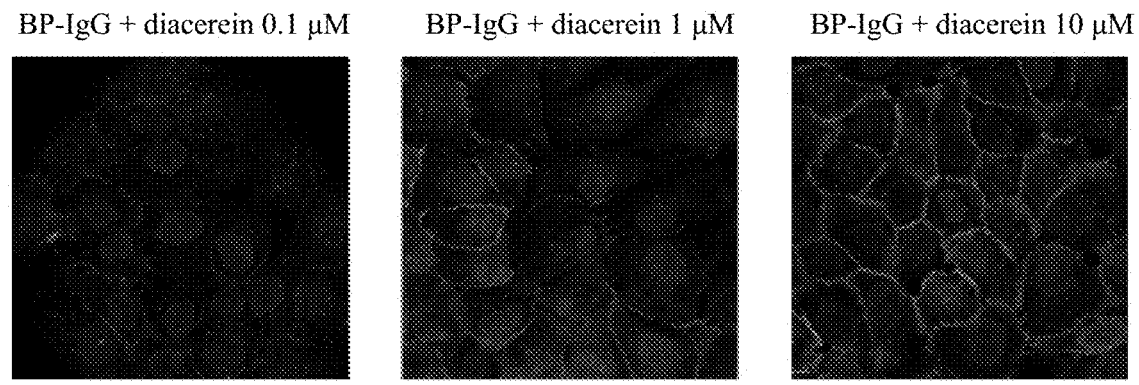
FIG. 6c shows confocal microscopy photographs of keratinocytes stained with fluorescence color and treated with IgG and diacerein at different concentrations.

Compared to control keratinocytes (i.e., not treated by IgG) and keratinocytes treated with Healthy-IgG (FIG. 6(a)), BP180 distribution in cell membrane appeared reduced and more diffuse in the cytoplasm of keratinocytes treated with BP-IgG suggesting occurrence of BP180 internalization induced by BP-IgG treatment (FIG. 6(b)). As diacerein concentration increased (0.1 to 10 μM), membranous localization of BP180 was restored, suggesting inhibition of BP180 internalization and maintenance of hemidesmosome integrity after diacerein treatment (FIG. 6(c)).

The results showed that diacerein and berberine are able to inhibit BP180 internalization, and thus may have treatment potential for BP.

The above disclosure is related to the detailed technical contents and inventive features thereof. People skilled in this field may proceed with a variety of modifications and replacements based on the disclosures and suggestions of the invention as described without departing from the characteristics thereof.

What is claimed is:

1. A method for treating an immunoinflammatory dermal disorder wherein said immunoinflammatory disorder is selected from the group consisting of dermatomyositis, bullous pemphigoid, pemphigus vulgaris, Behcet's disease, urticaria, and contact dermatitis, comprising administering to a subject in need thereof a pharmaceutical composition comprising a therapeutically effective amount of a compound selected from the group consisting of diacerein and rhein, or a pharmaceutically acceptable salt thereof.

2. The method of claim 1, wherein said immunoinflammatory dermal disorder is bullous pemphigoid.

3. The method of claim 1, wherein the compound is diacerein.

4. The method of claim 1, wherein the compound is the primary pharmaceutically active component.

5. The method of claim 1, wherein the compound is the only pharmaceutically active component.

6. The method of claim 1, wherein the subject is a human.

7. The method of claim 1, wherein said therapeutically effective amount of said compound is equivalent to 10 to 200 mg of diacerein base per day.

8. A method for preventing a relapse of bullous pemphigoid in a subject diagnosed with bullous pemphigoid, comprising administering to the subject a pharmaceutical composition comprising a therapeutically effective amount of a compound selected from the group consisting of diacerein and rhein, or a pharmaceutically acceptable salt thereof.

* * * * *